(12) United States Patent
Obermiller et al.

(10) Patent No.: US 8,986,338 B2
(45) Date of Patent: Mar. 24, 2015

(54) VASCULAR PLUGS

(75) Inventors: F. Joseph Obermiller, West Lafayette, IN (US); Michael D. Deckard, Solsberry, IN (US); Kathryn Evert, Bloomington, IN (US); Michael W. Hardert, Bloomington, IN (US)

(73) Assignees: Cook Biotech Incorporated, West Lafayette, IN (US); Cook Medical Technologies LLC, Bloomington, IN (US)

( * ) Notice: Subject to any disclaimer, the term of this patent is extended or adjusted under 35 U.S.C. 154(b) by 523 days.

(21) Appl. No.: 12/608,243

(22) Filed: Oct. 29, 2009

(65) Prior Publication Data

US 2010/0106178 A1  Apr. 29, 2010

Related U.S. Application Data

(60) Provisional application No. 61/109,323, filed on Oct. 29, 2008.

(51) Int. Cl.
| | |
|---|---|
| *A61F 2/06* | (2013.01) |
| *A61B 17/12* | (2006.01) |
| *A61B 17/00* | (2006.01) |

(52) U.S. Cl.
CPC ....... *A61B 17/12022* (2013.01); *A61B 17/0057* (2013.01); *A61B 17/12109* (2013.01); *A61B 17/12159* (2013.01); *A61B 17/12172* (2013.01); *A61B 17/12177* (2013.01); *A61B 17/1219* (2013.01); *A61B 2017/12054* (2013.01)
USPC .......................................... 606/192; 606/194

(58) Field of Classification Search
CPC ...................... A61B 17/12109; A61B 17/1214; A61B 17/12145; A61B 17/1215; A61B 17/12168; A61B 17/12172; A61B 17/12177; A61B 17/12181; A61B 17/1219
USPC ................. 606/135, 157, 192–194, 198, 200; 623/1.13, 1.24, 23.64–23.7
See application file for complete search history.

(56) References Cited

U.S. PATENT DOCUMENTS

| | | | | |
|---|---|---|---|---|
| 5,382,261 | A * | 1/1995 | Palmaz .......................... | 606/158 |
| 5,499,995 | A * | 3/1996 | Teirstein ........................ | 606/192 |
| 5,919,224 | A * | 7/1999 | Thompson et al. ............ | 606/200 |
| 6,312,407 | B1 * | 11/2001 | Zadno-Azizi et al. ......... | 606/198 |
| 6,589,256 | B2 * | 7/2003 | Forber ........................... | 606/151 |
| 2001/0039450 | A1 | 11/2001 | Pavcnik et al. | |

(Continued)

FOREIGN PATENT DOCUMENTS

| | | |
|---|---|---|
| EP | 1157663 | 11/2001 |
| WO | WO 00/51500 A | 9/2000 |

*Primary Examiner* — Kathleen Holwerda
*Assistant Examiner* — Sarah W Aleman
(74) *Attorney, Agent, or Firm* — Woodard, Emhardt, Moriarty, McNett & Henry LLP

(57) ABSTRACT

Certain aspects of the present invention provide devices for occluding vascular vessels. In some preferred forms, these devices are able to move from a first condition to a less compact, second condition in a vascular vessel so as to fully or partially prevent fluid from passing through the vessel. One such device includes a frame and a flexible sheet material. The device also includes an occluding material that is located in an interior region of the frame. The flexible sheet material and frame are associated with one another such that when the device is in the second condition in the vascular vessel, the sheet material is positioned in the vessel lumen so as to block fluid flow through the lumen.

31 Claims, 8 Drawing Sheets

(56) References Cited

U.S. PATENT DOCUMENTS

| | | |
|---|---|---|
| 2003/0139819 A1 | 7/2003 | Beer et al. |
| 2003/0171801 A1* | 9/2003 | Bates .......................... 623/1.13 |
| 2004/0143288 A1* | 7/2004 | Searle ........................... 606/200 |
| 2005/0096735 A1 | 5/2005 | Hojeibane |
| 2006/0212055 A1* | 9/2006 | Karabey et al. ................ 606/158 |
| 2007/0005083 A1 | 1/2007 | Sabanathan et al. |
| 2007/0292472 A1* | 12/2007 | Paul et al. ...................... 424/423 |
| 2008/0161936 A1* | 7/2008 | Feller et al. ................ 623/23.76 |

\* cited by examiner

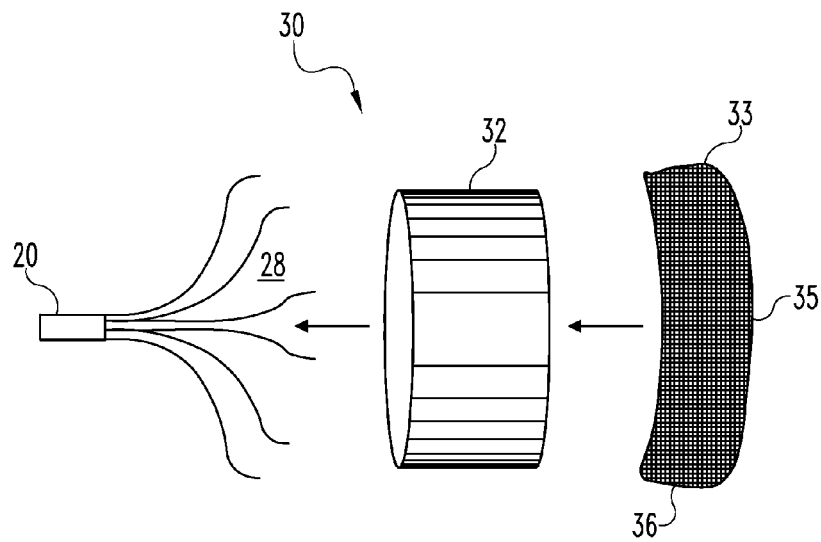
Fig. 2A
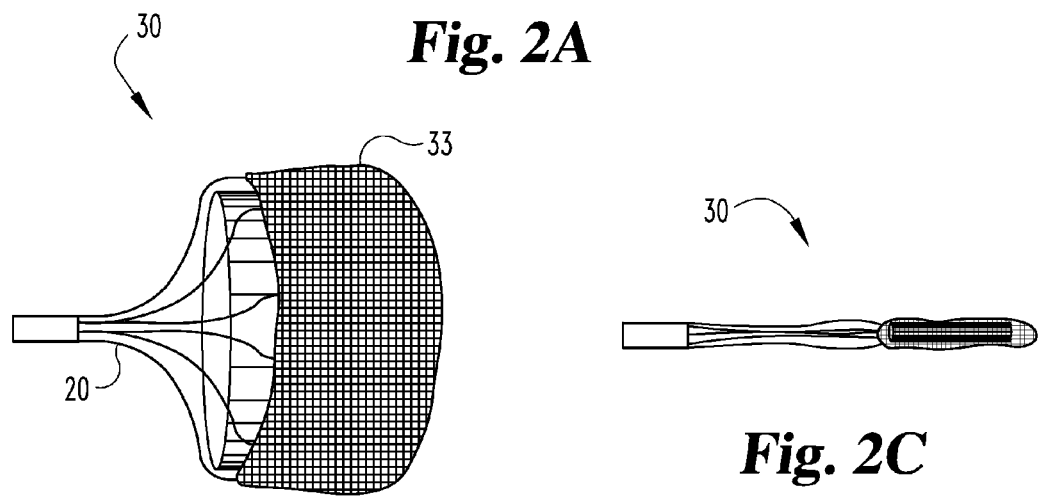
Fig. 2B
Fig. 2C
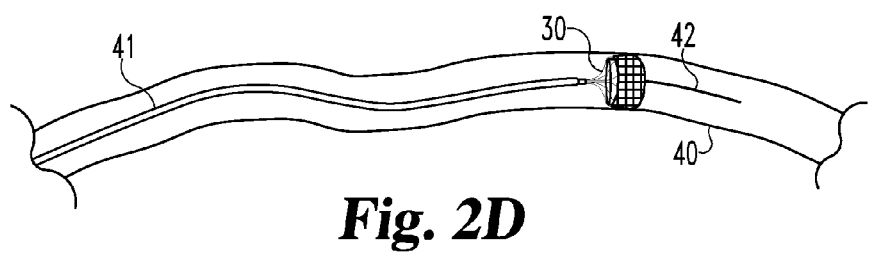
Fig. 2D

VASCULAR PLUGS

REFERENCE TO RELATED APPLICATION

The present application claims the benefit of U.S. Provisional Patent Application Ser. No. 61/109,323 filed Oct. 29, 2008 entitled "VASCULAR PLUGS" which is hereby incorporated by reference in its entirety.

BACKGROUND

The present invention relates generally to medical technology and in particular aspects to methods and devices for occluding bodily passageways.

As further background, there are a variety of reasons why those skilled in the art attempt to occlude or otherwise block fluid flow through vascular vessels and other openings and passageways in the body. In some instances, the desire is to treat an aneurysm, AV fistula or other blood vessel malformation. Although the prior art provides technology in this area, there remain needs for improved and/or alternative devices for occluding or otherwise blocking fluid flow through passageways and openings in the body, as well as methods for preparing and utilizing these devices. The present invention is addressed to those needs.

SUMMARY

The present invention provides, in certain aspects, unique devices and methods for occluding bodily vessels, and in certain embodiments, vascular vessels. One such device includes a frame and a flexible sheet material that is coupled to the frame. This device also includes an expandable occluding material that is located in an interior region of the frame and is effective to expand at the vessel site so as to provide an expanded material at the vascular site. The frame is movable between a first condition that is suitable for transluminal vascular delivery to a vascular site or other vessel site for providing an occluding device, and an expanded second condition that is adapted for deployment at the site. The frame has a proximal end and a distal end and includes a plurality of elongate arms. The arms emanate from a common centralized region at the proximal end of the frame, and extend distally to the distal frame end. The expanded second condition includes an expanded frame segment in which the arms are outwardly displaced relative to the common centralized region. The expanded frame segment is spaced distally from the common centralized region. The flexible sheet material is coupled to the frame such that when the frame is in the expanded second condition at the site, the sheet material is positioned in the vascular or other vessel lumen so as to block fluid flow through the lumen. In some inventive arrangements, the sheet material will extend across essentially the entire vessel lumen when the frame is in the expanded second condition at the site. The device, in some forms, will have one or more of the following features. The frame can be compressed when in the first condition. The frame can be self-expandable. The expandable material upon expansion at the vascular site can be effective to at least partially move the frame between the first condition and the expanded second condition. The device can be adapted so that the sheet material includes portions located between the arms of the expanded frame segment and inner wall surfaces of the vascular vessel when the frame is in the expanded second condition at the vascular site. The arms of the expanded frame segment can be located between the occluding material and inner wall surfaces of the vascular vessel when the frame is in the expanded second condition at the vascular site. The expanded frame segment can include a conical portion. The expanded frame segment can include a bulbous portion. At least part of the occluding material can be located externally of the frame when the frame is in the expanded second condition at the vascular or other vessel site. The flexible sheet material can be coupled to the frame such that when the frame moves from the first condition to the expanded second condition at the vascular site, the sheet material is drawn across at least part of the vascular or other vessel lumen.

In another embodiment, the invention provides a medical product for delivering an occlusive device to a vascular vessel. This particular product includes an endoluminally advanceable delivery device and an occlusive device that is removably positioned in a lumen of the delivery device. The occlusive device is configured for deployment from the delivery device lumen in the vascular vessel for occluding the vessel. The occlusive device includes a frame, an expandable occluding material that is located in an interior region of the frame, and a flexible sheet material that is coupled to the frame. The occlusive device is compressible to a compressed first condition for positioning the occlusive device in the delivery device lumen. When in the compressed first condition, the occlusive device is expandable to an expanded second condition upon deployment from the delivery device in the vascular vessel. In the expanded second condition, the occluding material and the frame are expanded such that the flexible sheet material is positioned across at least part of the vascular vessel so as to block fluid flow through the vessel. In the expanded second condition as well, the occlusive device contacts inner wall surfaces of the vascular vessel and occludes the vessel, with portions of the frame being located between the expanded occluding material and the inner wall surfaces of the vascular vessel. The product, in some forms, will have one or more of the following features. The product can further include a deployment member that is translatable through the delivery device lumen for deploying the occlusive device from the delivery device lumen. This deployment member can be adapted for coupling to the occlusive device for pulling the occlusive device through the vascular vessel. The occlusive device can further include a coupling element extending proximally from the proximal end of the frame. This coupling element can include a hook. The occlusive device can be configured for over-the-wire delivery. The occluding material can be compressed when the occlusive device is in the compressed first condition. The product can be adapted so that the sheet material extends distally from the frame when the occlusive device is in the compressed first condition. The product can be adapted so that the occluding material and the sheet material contact one another across a portion of the vascular vessel when the occlusive device is in the expanded second condition at the vascular site.

One aspect of the present invention provides a device for occluding a vascular vessel that includes a frame and a flexible sheet material that is coupled to the frame. This specific illustrative device also includes an expandable material that is located in an interior region of the frame and is effective to expand at the vascular site so as to provide an expanded material at the vascular site. The frame is movable between a first condition suitable for transluminal vascular delivery to a vascular site for providing an occluding device, and an expanded second condition that is adapted for deployment at the vascular site. The expanded second condition includes a first frame perimeter having an opening in the vascular vessel lumen when the frame is deployed at the vascular site. In some designs, this frame opening essentially will be concentric with the vascular vessel lumen when the frame is deployed at the vascular site. The flexible sheet material is coupled to the frame such that when the frame is in the expanded second condition at the vascular site, the sheet material is positioned across all or part of the first frame perimeter opening. In some embodiments, the flexible sheet material will be coupled to the frame such that when the frame moves from the first condition to the expanded second condition in the vascular vessel, the sheet material will be drawn across all or part of the first frame perimeter opening. The device, in some forms, will have one or more of the following features. The first frame perimeter opening can be adjacent the interior region of the frame. The first frame perimeter opening can have a diameter that is essentially equal in size to that of the vascular vessel lumen when the frame is in the expanded second condition at the vascular site. The first frame perimeter opening can be located at the distal end of the frame. The expanded second condition can further include a second frame perimeter opening that is spaced proximally from the first frame perimeter opening. The first frame perimeter opening can have a larger diameter than the second frame perimeter opening. The expanded material can occur proximally of the sheet material when the frame is in the expanded second condition at the vascular site. The expanded material can occur distally of the sheet material when the frame is in the expanded second condition at the vascular site. The device can be configured so that the first frame perimeter opening is concentric with the vascular vessel lumen when the frame is deployed at the vascular site.

Another inventive occluding device comprises a frame, an expandable occluding material, and a flexible sheet material that is coupled to the frame. The frame is movable between a first condition that is suitable for transluminal vascular delivery to a vascular site for providing an occluding device, and an expanded second condition that is adapted for deployment at the vascular site. The frame has an interior space that expands as the frame moves from the first condition to the second condition, with the expanded second condition including an expanded interior space adjacent to a distal frame opening. The expandable occluding material is located in the interior space of the frame, and is effective to expand at the vascular site so as to provide an expanded material at the vascular site. The flexible sheet material is coupled to the frame such that when the frame is in the expanded second condition at the vascular site, the sheet material is positioned across all or part of the distal frame opening. In some embodiments, the positioning of the sheet material across this opening will be at least partially responsible for retaining the occluding material in the interior space. The device, in some forms, will have one or more of the following features. The distal frame opening and at least part of the expanded interior space can have essentially the same diameter. The flexible sheet material can comprise collagen. The flexible sheet material can include a harvested extracellular matrix sheet material. The flexible sheet material can comprise a synthetic polymeric material. The flexible sheet material can include Dacron.

A further embodiment of the invention provides a device for occluding a vascular vessel that is movable between a first condition suitable for transluminal vascular delivery to a vascular site for providing an occluding device, and an expanded second condition adapted for deployment at the vascular site. The device comprises a tube that is formed with a flexible sheet material. The tube has a first end portion, a second end portion and a wall defining an interior region. The device further includes an expandable occluding material that is located in the interior region of the tube. The device further includes a first expandable frame member which is located at the first end portion of the tube, and a second expandable frame member which is located at the second end portion of the tube. The device is configured so that upon deployment at the vascular site, the expanded second condition includes the first frame member, the second frame member and the occluding material expanded so as to force the tube into contact with inner wall surfaces of the vascular vessel wherein fluid flow through the vessel is blocked. The device, in some forms, will have one or more of the following features. The sheet material can be receptive to tissue ingrowth. The sheet material can be remodelable. The first expandable frame member and the second expandable frame member can each include a plurality of elongate arms that extend away from the first end portion and the second end portion of the tube, respectively. The plurality of elongate arms in the first expandable frame member and the second expandable frame member can extend toward a first common centralized region and a second common centralized region, respectively. The first expandable member and the second expandable member can be attached to the first end portion and the second end portion of the tube, respectively, along the perimeters of the respective tube end portions.

In another embodiment, the invention provides a device for occluding a vascular vessel that includes a frame and a flexible sheet material that is coupled to the frame. This device also includes an expandable occluding material that is located in an interior region of the frame and that is effective to volumetrically expand at the vascular vessel site so as to provide a volumetrically expanded material at the vascular vessel site. The frame is movable between a first condition suitable for transluminal vascular delivery to a vascular vessel site for providing an occluding device, and an expanded second condition adapted for deployment at the vascular vessel site. The frame has a proximal end and a distal end and including a plurality of elongate arms that emanate from a common centralized region at the proximal end of the frame and extend distally to the distal frame end. The expanded second condition includes an expanded frame segment in which the arms of the frame are outwardly displaced relative to their positioning in the first condition of the frame. The expanded frame segment is spaced distally from the common centralized region. The flexible sheet material is coupled to the frame such that when the frame is in the expanded second condition at the vascular vessel site, the sheet material is positioned in the vascular vessel lumen so as to block fluid flow through the lumen.

In yet another embodiment, the invention provides a medical product for delivering an occlusive device to a vascular vessel. This particular device includes an endoluminally advanceable delivery device and an occlusive device that is removably positioned in the lumen of the delivery device. The occlusive device is configured for deployment from the delivery device lumen in the vascular vessel for occluding the vessel. The occlusive device includes a frame, an expandable occluding material that is located in an interior region of the frame, and a flexible sheet material that is coupled to the frame. The occlusive device is compressible to a compressed first condition for positioning the occlusive device in the delivery device lumen, and when in the compressed first condition the occlusive device is expandable to an expanded second condition upon deployment from the delivery device in the vascular vessel. When the occlusive device is in the expanded second condition in the vascular vessel, the occluding material and the frame are both radially expanded relative to their respective positions in the first condition of the occlusive device, with the flexible sheet material positioned across at least part of the vascular vessel so as to block fluid flow through the vessel with the occlusive device contacting inner wall surfaces of the vascular vessel and occluding the vessel and with portions of the frame being located between the expanded occluding material and the inner wall surfaces of the vascular vessel.

In another embodiment, the invention provides a device for occluding a vascular vessel that includes a frame and a flexible sheet material that is coupled to the frame. This particular device also includes an expandable material that is located in an interior region of the frame and is effective to volumetrically expand at the vascular vessel site so as to provide a volumetrically expanded material at the vascular vessel site. The frame is movable between a first condition suitable for transluminal vascular delivery to a vascular vessel site for providing an occluding device, and an expanded second condition adapted for deployment at the vascular vessel site. The expanded second condition includes a first frame perimeter defining an opening in the frame. The flexible sheet material is coupled to the frame such that when the frame is in the expanded second condition at the vascular vessel site, the sheet material is positioned across the frame opening.

In yet another aspect, the invention provides a device for occluding a vascular vessel that includes a frame, an expandable occluding material and a flexible sheet material that is coupled to the frame. The frame is movable between a first condition that is suitable for transluminal vascular delivery to a vascular vessel site for providing an occluding device, and an expanded second condition adapted for deployment at the vascular vessel site. The frame having an interior space that expands as the frame moves from the first condition to the second condition. The expanded second condition includes an expanded interior space adjacent to a distal frame opening. The expandable occluding material is located in the interior space of the frame and is effective to volumetrically expand at the vascular vessel site so as to provide a volumetrically expanded material in the vascular vessel. The flexible sheet material is coupled to the frame such that when the frame is in the expanded second condition at the vascular vessel site, the sheet material is positioned across the distal frame opening.

Yet another aspect of the present invention provides a device for occluding a vascular vessel that is movable between a first condition that is suitable for transluminal vascular delivery to a vascular vessel site for providing an occluding device, and an expanded second condition adapted for deployment at the vascular vessel site. The device includes a tube that is formed with a flexible sheet material. The tube has a first end portion, a second end portion and a wall defining an interior region. The device further includes an expandable occluding material that is located in the interior region of the tube. The device further includes a first expandable frame member that is located at the first end portion of the tube and a second expandable frame member that is located at the second end portion of the tube. The first frame member, the second frame member and the occluding material are all effective to expand upon being deployed in the vascular vessel so as to force the tube into contact with inner wall surfaces of the vascular vessel for blocking fluid flow through the vessel.

In another embodiment, the invention provides an occlusion device that is deliverable to a vascular vessel in a compressed condition and thereafter expandable in the vessel to an expanded condition for occluding the vessel. The occlusion device includes a remodelable ECM construct that is effective to volumetrically expand in the vessel so as to provide a volumetrically expanded mass of remodelable ECM material in the vessel. The device further includes a frame assembly that is at least partially embedded in the remodelable ECM construct. The frame assembly includes a deformable distal frame member, a deformable proximal frame member and a connector that extends therebetween to connect the distal frame member to the proximal frame member.

Other objects, embodiments, forms, features, advantages, aspects, and benefits of the present invention shall become apparent from the detailed description and drawings included herein.

BRIEF DESCRIPTION OF THE DRAWINGS

FIG. 2A shows an unassembled version of an occlusion device according to one embodiment of the present invention.

FIG. 2B shows the occlusion device of FIG. 2A assembled and in an expanded condition.

FIG. 2C shows the occlusion device of FIG. 2A assembled and in a compressed condition.

FIG. 2D shows a step in one inventive method in which the occlusion device of FIGS. 2A-2C is being deployed in a vascular vessel.

DETAILED DESCRIPTION

Figure 1A:
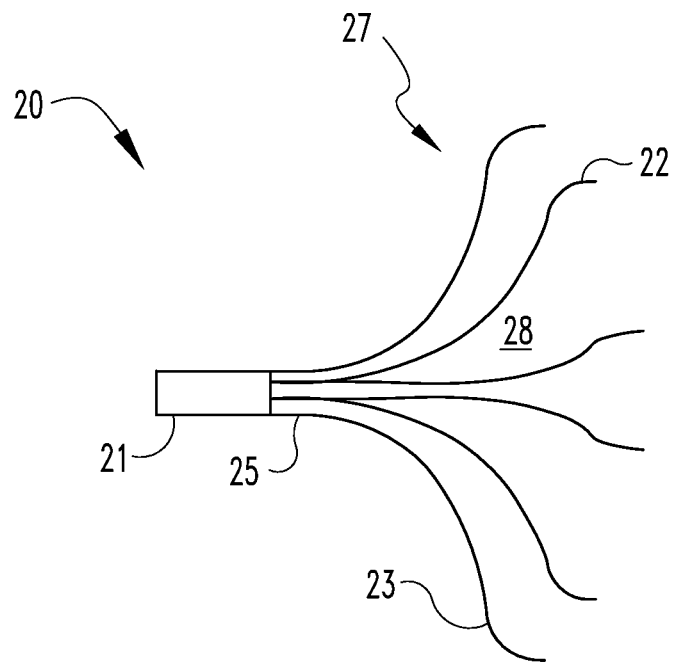
FIG. 1A is a perspective view of a frame useful in certain aspects of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique devices for occluding vascular vessels.

In some preferred forms, these devices are able to move from a first condition to an expanded or otherwise less compact second condition in a vascular vessel so as to at least partially block fluid flow in the vessel, and in some cases, to completely prevent fluid from passing through the vessel. Some of these devices are configured to be somewhat compressible so that they can be folded and/or rolled or otherwise compressed into a low-profile condition for delivery through the vasculature, for example, in a catheter lumen. When deployed from the catheter, these devices transform in the vessel to provide a unique blocking arrangement there even when considerable forces act to dispel the device from its deployed location. The invention further provides methods for preparing these and other occlusion devices, as well as medical products that include such devices enclosed within sterile packaging.

Some inventive devices include an expandable material that is effective to expand at a vascular vessel site so as to at least partially fill the site with an expanded material. These devices also include sheet or sheet-like material(s) and one or more frame members arranged in and/or around the material. In some forms, the expanded material itself is effective to essentially block fluid flow through the vessel, and the addition of the sheet and frame components enhances the overall blockage, for example, by helping to anchor the expanded material, providing support to the material, protecting the material and/or otherwise providing assistance to the material to enable a more effective blockage. In other forms, the expanded material itself is not effective to fully block fluid flow through the vessel; full blockage is achieved through the addition of the sheet and frame components. In one particular embodiment, a combination of sheet and frame components itself is effective to essentially block fluid flow through the vessel, and the addition of the expanded material enhances the overall blockage. There are some inventive devices in which an occluding material is fully or partially contained within a sheet-frame combination. Yet even in these forms, passages and other openings in the sheet-frame combination expose the occluding material to nearby tissues at the vascular site. With certain designs, expandable materials will pass through these openings as they expand so as to make significant contact with interior surfaces of the vessel wall.

Various types of frame and frame-like elements can be utilized in the present invention. These include single- and multiple-part devices. In some forms, a frame member will include a filament or wire body or other similar frame or frame-like support structure. Frame members, in some embodiments, can be designed to move between a first condition and one or more other conditions, for example, in the case of a frame that is compactable to a compacted, first condition, and when in this compacted condition, is then expandable to an expanded, second condition. In forms where a frame has the capacity to expand, these frames can include those that are considered self-expanding and those that require at least some manipulation in order to expand.

Frames of this sort and other similar support elements useful in the present invention can be constructed using one or more pieces of superelastic wire or any of a variety of other suitable materials described herein or otherwise known to those skilled in the art including MRI compatible materials. Frames and other similar expandable and non-expandable support members, when utilized in the present invention, may be made from metallic or non-metallic material, or both. The non-metallic material can suitably be a synthetic polymeric material, including for example bioresorbable and/or non-bioresorbable plastics. Materials commonly used in medical device construction include biologically compatible metals, e.g., stainless steel, titanium, tantalum, gold, platinum, copper and the like, as well as alloys of these metals; synthetic polymeric materials; low shape memory plastic; a shape-memory plastic or alloy, such as nitinol; and the like.

In certain forms, a resilient frame member can be provided in a relaxed condition. The frame can then be deformed (e.g., collapsed, compressed, etc.) from this relaxed, first condition to a deformed, second condition and held there. In this deformed, second condition, the resilient frame is then poised to essentially return to its relaxed, first condition. Illustratively, a frame can be compressed into a compressed condition (e.g., by folding one or more times and/or rolling portions of the frame) for positioning in a delivery device lumen having a relatively smaller diameter than that which the frame could otherwise fit in its relaxed condition. In this compressed condition, the frame then has the ability to self-expand essentially back to its prior, relaxed condition upon being removed from the delivery device lumen. In other embodiments, frame members and other frame-like elements exhibit little or no resiliency.

In some instances, a frame element will be urged to expand by another device component exerting force on the frame element as the component expands. This can be made to occur with both self expanding and non-self expanding frame elements. Frames can be provided and delivered in a contracted state, and then expanded upon the application of a force, e.g. an outward radial force, to the frame. Illustratively, an outward force can be provided by an expandable material positioned in and/or around a frame structure. Frame structures which take on a contracted state, but expand in response to a conditional change, e.g., a change in temperature such as may be incurred in a temperature transition from a first temperature below the body temperature of a patient, to the body temperature of the patient, can also be utilized. Frame members having these or other characteristics may be used in embodiments of the present invention.

Figure 1B:
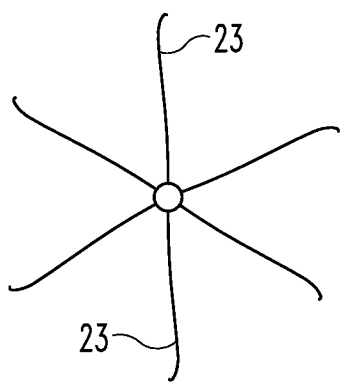
FIG. 1B is a front view of the frame of FIG. 1A.

With reference now to FIG. 1A, shown is a perspective view of a self-expandable frame 20 useful in certain aspects of the present invention. Frame 20 has a proximal end 21 and a distal end 22, and includes a plurality of elongate arms 23. Arms 23 emanate from a common centralized region 25, and extend distally from there to the distal end 22 of the frame. Frame 20 is shown in an expanded condition in FIG. 1A. This expanded condition includes an expanded frame segment 27 in which the plurality of arms 23 are outwardly displaced relative to common centralized region 25. As can be seen in FIG. 1B, as the arms extend from common centralized region 25 toward the distal end 22 of the frame, they also extend radially outward. Accordingly, in this particular embodiment, the distal end of the frame is open, and provides access to an interior space 28 in the frame. Arms 23, while exhibiting curvature as they extend toward the distal end of the frame, could also be made to extend in a variety of other non-straight fashions, or to be straight. When in an expanded condition, frame 20 can be compressed to a compressed condition that is suitable for delivering the frame to a vascular site for providing an occluding device. At the vascular site, frame 20 can be deployed and thus caused or allowed to expand.

Frame 20 can be incorporated into a variety of inventive devices. FIG. 2A shows one such device 30 in an unassembled condition. In addition to frame 20, occlusion device 30 includes an expandable occluding material 32 and a flexible sheet material 33. Flexible material 33 can be formed with one or more of a variety of sheet or sheet-like materials including some that are naturally derived and some that are non-naturally derived as discussed in more detail below. In some preferred embodiments, a sheet material such as sheet material 33 is formed with a collagen-containing material such as a harvested collagenous ECM material. Additionally or alternatively, a sheet material can include a synthetic polymeric material such as Dacron.

Occluding material 32 can be formed with one or more of a variety of materials as well, and is effective to expand at the vascular site so as to provide an expandable material at the vascular site, and in some instances, essentially filling the vascular site with an expanded material. In some preferred embodiments, an occluding material such as material 32 comprises a highly-expandable collagenous material. At least a portion of occluding material 32 can be inserted into the interior frame space 28 through the distal, open end of the frame as indicated by the left-most arrow in FIG. 2A. Sheet material 33 can then be placed over the occluding material and attached to or otherwise associated with the frame, although it could additionally or alternatively be attached to the occluding material. In this particular embodiment, sheet material 33 has an end 35 and a side wall 36 so as to provide a covering generally in the shape of a bowl or cup. In this regard, the shaped or otherwise non-planar covering can be placed over the occluding material-frame combination and attached to the frame so that the occluding material is located between parts of the frame and the covering.

FIG. 2B shows the occlusion device of FIG. 2A after it has been assembled. In this condition, at least part of the occluding material 32 is positioned in interior frame space 28. In some forms, essentially all of the occluding material will occur between the proximal and distal ends of a frame of this type. In other forms, part of the occluding material will extend beyond the proximal and/or distal end of a frame member. In this particular embodiment, the shaped covering is received over the occluding material-frame combination such that distal portions of the frame arms are located between the occluding material and the side wall 36 of the covering. In this regard, the frame-covering combination essentially contains the occluding material.

FIG. 2C shows the assembled device 30 in a compressed condition. Compressing the device in this manner is useful for fitting the device into a delivery device for transluminal vascular delivery. In such a reduced-diameter condition, the frame and occluding material are both compressed, with at least part of the compressed occluding material located within the compressed frame. The flexible sheet material is also compressed or otherwise forced into a more compact condition along with the other components. In a compressed device, the sheet material may roll and/or fold over itself and/or the other device components one or more times. In such a compact condition, the device will be able to travel through bodily passageway which it otherwise would not have been able to pass (or pass as easily).

FIG. 2D shows a step in one illustrative inventive method in which the occlusion device of FIG. 2C is being deployed in a vascular vessel 40. Prior to this step, the occlusion device is compressed and removably positioned in a lumen of a delivery device 41. The delivery device is then advanced through the vascular vessel over an emplaced guidewire 42. Once at a desired location, the device is deployed from the delivery device lumen, over the guidewire and into the vascular vessel, whereupon the device expands to block flow through the vessel. Although more than one inventive device can be deployed in a vascular region, in certain peripheral and non-peripheral vascular settings, a single inventive device can be effective to occlude a passage that would have otherwise required many embolic coils, or that can not be effectively treated with coils or other embolic devices, for example, as occurs with some giant aneurysms and other malformations. Inventive device can be sized to occlude bodily passageways having diameters ranging from about 2 mm to about 22 mm or more. When an inventive device is used to treat an aneurysm, AV fistula or other blood vessel malformation in the brain or other part of the body, the device may be placed at a variety of locations relative to the malformation. In some instances, a device may be positioned somewhat away the malformation so that it blocks blood flow to the affected area. Additionally or alternatively, an inventive device can be placed in affected area, for example, in situations where a device is placed in and around a fistula tract or an aneurysm neck.

Continuing with FIG. 2D, the sheet material is coupled to the frame such that when the frame moves from a first condition to an expanded second condition at the vascular site, the sheet material is pulled therealong and into a blocking arrangement in the lumen, for example, with at least the end 35 of the sheet material extending across the lumen between its walls. This blocking arrangement is effective to at least partially block fluid flow through the lumen. In such a blocking arrangement, portions of the sheet material including side wall 36 can extend along surfaces of the vessel wall to provide enhanced blocking, and in some cases, complete sealing off of the vessel lumen. While not necessary to broader aspects of the invention, in some forms, upon deployment, the sheet material will be located between the frame member and the vessel wall so as prevent contact between the frame member and vessel wall. In other forms, the frame member and/or occluding material, upon deployment, will contact the vessel wall. The guidewire and delivery device are then withdrawn, leaving the deployed device behind in the vessel.

In some preferred embodiments, a sheet or sheet-like material will be coupled to a frame such that when the frame moves from a first condition to an expanded second condition at the vascular site, the sheet material will be forced into a blocking arrangement in the lumen with material extending across a substantial portion of the lumen. A sheet material, whether extending fully or partially across the lumen, can occur upstream and/or downstream of an occluding material in a deployed device. In some devices, a sheet material will occur between a first occluding material component and a second occluding material component. These types of unique relationships between sheet materials and occluding materials can enhance the type of occlusion achieved.

A first device component can act to shield or otherwise protect a second device component at an occlusion site. Illustratively, an upstream sheet material can reduce or eliminate any deleterious effects of oncoming fluids on a downstream occluding material. Creating these types of protected environments can enhance the overall occlusive result, particularly in situations where the protected component can use that protection to achieve a result that it otherwise would not have been able to achieve. Protection can be provided upstream and/or downstream. In some cases, protection from the forces of oncoming fluids can help prevent migration of the device, or a device component. A protected environment can also increase the amount of time an incorporated substance (e.g., a drug coating, occluding hydrogel, etc.) remains at the occlusion site.

It may be particularly advantageous to create a protected environment to shield or otherwise protect early clot development in environments where blood components are present, and if a device is receptive to tissue ingrowth, to protect early tissue formation occurring at the occlusion site. When an inventive device incorporates a remodelable material, a protected environment can enhance this material's ability to remodel. Referring again to FIG. 2D, if device 30 is deployed such that sheet material 33 is positioned upstream of proximal frame end 21, at least the end 35 of the material will be in a position to shield the occluding material 32 from any oncoming fluids. If occluding material 32 is receptive to tissue ingrowth, this sort of shielding can provide a more effective environment for the tissue ingrowth to take place. In some forms, both occluding material 32 and sheet material 33 will be comprised of tissue ingrowth receptive materials. Upon deployment of such a device in accordance with the present invention, cells from the patient can infiltrate the material, leading to, for example, new tissue growth on, around, and/or within the device. In some embodiments, one or more device components will be comprised of a remodelable material. In these embodiments, the remodelable components promote and/or facilitate the formation of new tissue, and are capable of being broken down and replaced by new tissue in such a way that the filling of a space by a deployed device is maintained throughout the remodeling process so as to eventually fill the space with new tissue.

Figure 3A:
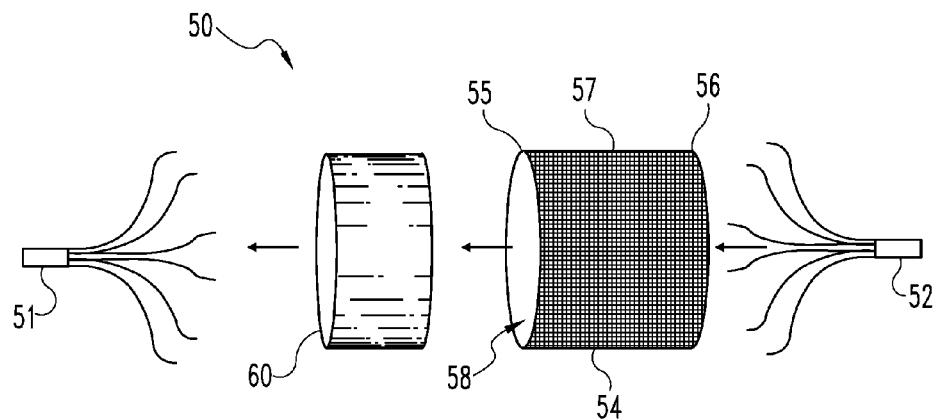
FIG. 3A shows an unassembled version of an occlusion device according to another embodiment of the present invention.

Inventive devices can incorporate one or more individual frame pieces. With reference now to FIG. 3A, shown is an unassembled version of an occlusion device 50 that includes two of the frame members from FIGS. 2A-2D. In addition to a first expandable frame member 51 and a second expandable frame member 52, device 50 includes a tube 54. Tube 54 is formed with a flexible sheet material (e.g., a mesh material) and has a first end 55, a second end 56 and a wall 57 defining an interior region 58. In some forms, the tube will be configured to elongate when decreasing in diameter. Device 50 further includes an expandable occluding material 60 that is effective to expand at the vascular site so as to provide an expanded material at the vascular site. As indicated by the series of arrows in FIG. 3A, the various components can be assembled to arrive at the device of FIG. 3B which is shown in an expanded condition. In this condition, occluding material 60 is positioned in the interior region 58 of the tube. First expandable frame member 51 and second expandable member 52 extend from the first tube end and the second tube end, respectively, with each providing a framework at the ends of the tube.

Figure 3B:
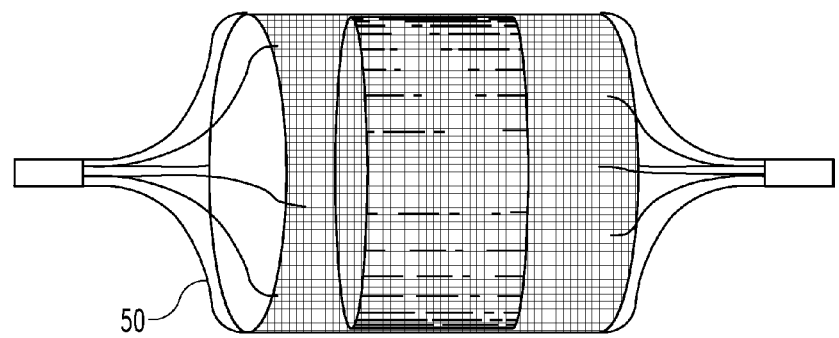
FIG. 3B shows the occlusion device of FIG. 3A assembled and in an expanded condition.
Figure 3C:
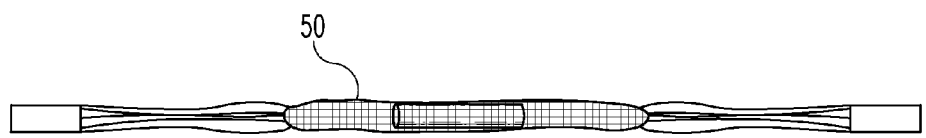
FIG. 3C shows the occlusion device of FIG. 3A assembled and in a compressed condition.

FIG. 3C shows device 50 in a more compact condition relative to what is shown in FIG. 3B. In this condition, the tube, frame and occluding material all exhibit a reduced diameter to facilitate transluminal vascular delivery to a vascular site. To achieve such a compact configuration, any part of the device (e.g., the tube) may roll and/or fold itself and/or another device part one or more times. Device 50 is configured so that upon deployment at a vascular site the first frame member, the second frame member and the occluding material expand so as to force the tube into contact with inner wall surfaces of the vascular vessel, which in some cases, will be effective to create a seal between the device and the vessel wall. In some instances, enough radial force will be exerted on the vessel wall to keep the device deployed there without the need for a separate anchoring system, although various anchoring adaptations can be incorporated into the device as discussed elsewhere herein.

Figure 4A:
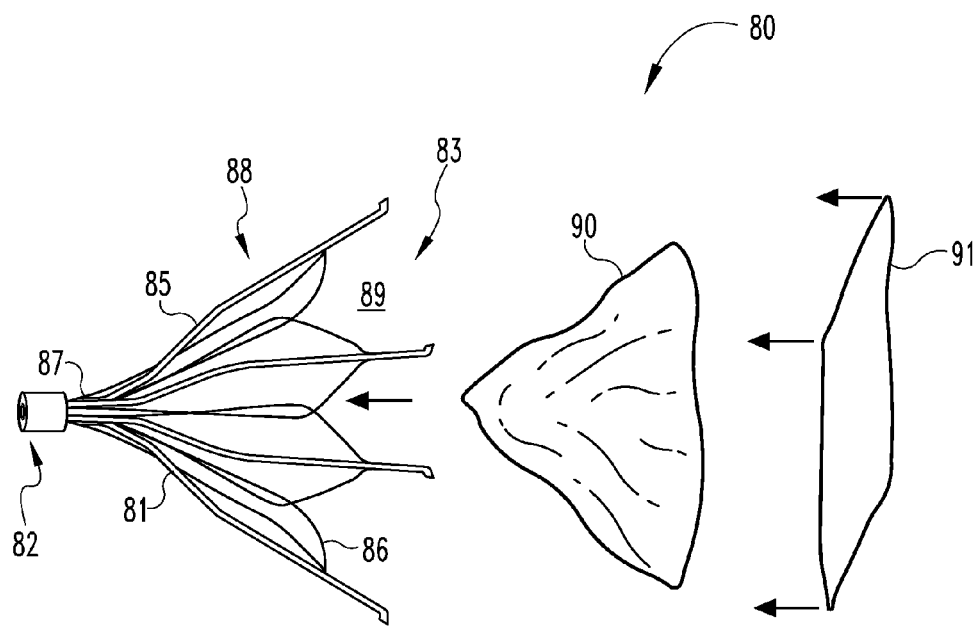
FIG. 4A shows an unassembled version of an occlusion device according to yet another embodiment of the present invention.

FIG. 4A shows another inventive occlusion device 80 in an unassembled condition. Device 80 includes a self-expandable frame 81 having a proximal end 82 and a distal end 83. Frame 81 includes a plurality of elongate arms 85 and optional supporting members 86. Arms 85 emanate from a common centralized region 87, and extend distally from there to the distal end 83 of the frame. Frame 81 is shown in an expanded condition in FIG. 4A. This expanded condition includes an expanded frame segment 88 in which the plurality of arms 85 are outwardly displaced relative to common centralized region 87. As the arms extend from common centralized region 87 toward the distal end 83 of the frame, they also extend radially outward from region 87. Accordingly, in this particular embodiment, the distal end of the frame is open, and provides access to an interior space 89 in the frame. When in an expanded condition, frame 81 can be compressed to a compressed condition that is suitable for delivering the frame to a vascular site for providing an occluding device. At the vascular site, frame 81 can be caused or allowed to expand upon deployment.

Device 80 also includes an occluding material 90 and a flexible sheet material 91. In this specific illustrative embodiment, occluding material 90 is effective to highly expand at the vascular site. In alternative embodiments, occluding materials such as that shown in FIG. 4A will be comprised of lesser-expandable or non-expandable materials yet will promote and/or facilitate vessel occlusion. Illustratively, an occluding material may be provided by a flowable material such as a collagenous hydrogel material. As indicated by the left-most arrow in FIG. 4A, the occluding material 90 is insertable into the interior frame space 89 through the distal, open end of the frame. Sheet material 91 can then be positioned adjacent the occluding material and coupled to the frame, the occluding material, or both. When occluding materials are capable of retaining shape, these materials can be shaped and configured in a variety of manners for use in the present invention. These include various three-dimensional shapes having rectilinear and/or curvilinear features. Suitable three-dimensional rectilinear shapes can have any suitable number of sides, and can include, for example, cubes, cuboids, tetrahedrons, prisms, pyramids, wedges, and variations thereof. Suitable three-dimensional curvilinear shapes can include, for example, spheres, spheroids, ellipsoids, cylinders, cones, and any suitable variations thereof (e.g., a segment of a sphere, or a truncated cone, etc.).

Figure 4B:
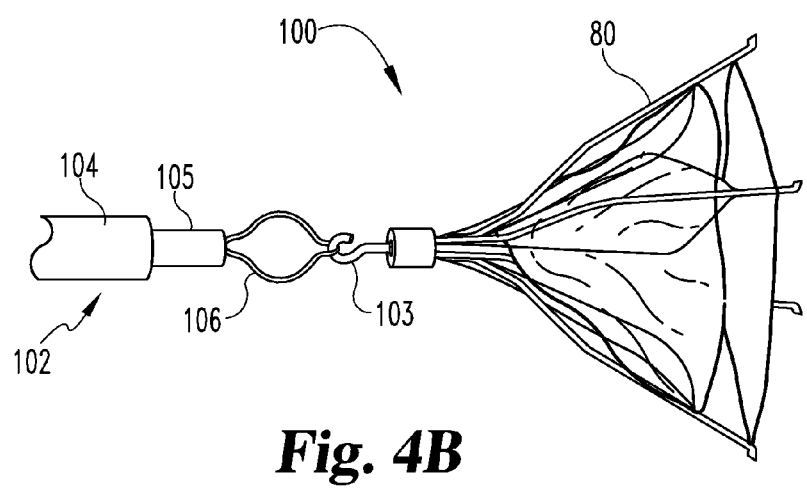
FIG. 4B shows an inventive medical product incorporating an assembled version of the occlusion device of FIG. 4A.

FIG. 4B shows an inventive medical product 100 that includes a delivery device 102 in association with an assembled version of device 80. In this particular embodiment, occluding material 90 and sheet material 91 are both located in interior frame space 89, with the sheet material sutured or otherwise attached to the frame. In this regard, the occluding material is essentially contained within the frame-sheet combination, although there are openings in this combination which will expose the material to the vascular surroundings upon deployment. Device 80 includes a hook 103 that extends proximally from common centralized region 87. Hook 103 provides a means by which the occlusion device can be releasably grasped by delivery device 102, although a variety of other hook and non-hook elements are contemplated in this regard.

Delivery device includes a cannulated sheath 104, and a deployment member 105 that is translatable through the sheath. FIG. 4B shows device 80 located externally of the sheath, although it is capable of being compressed and removably positioned in the sheath lumen. A resilient element 106 extends distally from deployment member 105. Resilient element may extend from the deployment member in a fixed manner, or alternatively the delivery system may be configured so that the resilient element fully or partially retracts within the member. The resilient element provides an opening through which hook 103 can pass for releasably engaging device 80 and deployment member 105. Retracting the resilient element within sheath 104 (or within the deployment member if so equipped) deforms the elements and forces the opening to compress around the hook.

When engaged, the deployment member 105 can be used in a variety of deployment and post-deployment steps. Illustratively, the member may be used to force the device from the sheath, as well as retract the device back into the sheath if desired. The member may also be used to reposition or otherwise manipulate the deployed device in the vessel, for example, by twisting the device and/or moving it back and forth in the vessel. In some cases, portions of the frame or other device adaptations will be effective to abrade inner surfaces of the vessel wall upon contact, and manipulations of this sort can be used to cause a desirable abrasion. Because the point of engagement between the occluding device and the deployment member occurs in a centralized region of the device (e.g., at hook 103), engaging and disengaging the components can occur away from the walls of the vessel.

Deployed devices, in certain embodiments, will provide one or more frame elements at or near the periphery of the device for contacting interior wall surfaces of the vascular vessel for anchoring and other purposes. The distal tips of elongate arms 85 provide this type of arrangement as shown in FIG. 4B. In some instances, parts of a device will embed themselves in the vessel wall upon deployment and/or any subsequent repositioning of the device in the vessel. As well, any number of other anchoring adaptations, barbs, ribs, protuberances, and/or other suitable surface modifications can be incorporated into an inventive device to roughen, condition, or otherwise de-epithelialize at least a portion of the vessel wall during and/or after deployment of the device within the vessel. The conditioning of the vessel wall tissue can serve to initiate a localized healing response in patient tissue that can be advantageous in enhancing the ingrowth of patient tissue into an inventive device, such as a device that is comprised of a tissue ingrowth receptive material.

Figure 4C:
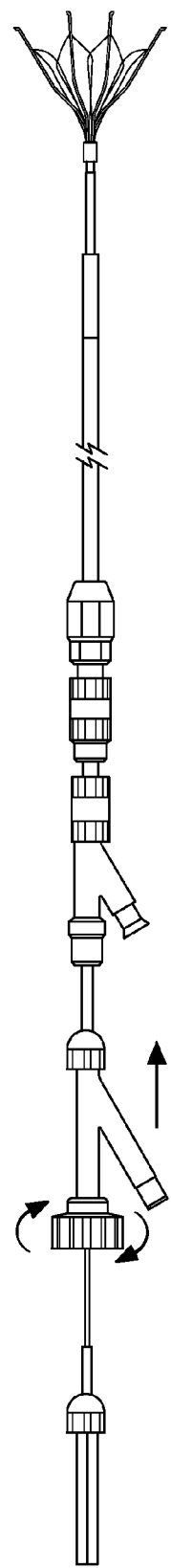
FIG. 4C shows another inventive medical product incorporating an assembled version of the occlusion device of FIG. 4A.

Various types of sheaths and other delivery devices can be utilized in the present invention. FIG. 4C shows a side view of one specific illustrative delivery device that can be used to deliver an inventive occlusion device to a vascular vessel site. In general, these devices will provide space (e.g., a lumen) into which one or more occlusion devices can be placed for delivery into the body. Certain preferred devices will include a lumen communication with a distal, open end. Commercially available catheters and other endoluminally advancable devices may be used in this regard.

Continuing now with additional discussion of frame shapes and configurations, in some forms, a frame member provides an elongate frame body having either a constant or varying cross-sectional area along its length, or portions thereof. Illustratively, all or part of a frame body can exhibit a generally cylindrical shape, a conical shape, and other suitable shapes including some having tapered and/or non-tapered longitudinal portions. As well, a cross section of a particular frame body portion can exhibit a variety shapes including some that have rectilinear and/or curvilinear features. Thus, a frame body can include a portion having a generally circular or non-circular (e.g., elliptical, square, star-shaped, hexagonal, etc.) cross section.

In some configurations, a frame member will be constructed such that upon deployment in a vascular vessel, portions of the frame will be positioned generally around the periphery of the vessel, either contacting the vessel wall or nearly contacting the vessel wall. These peripheral frame portions, when viewed from an end of the device (e.g., as shown in FIG. 1B), will provide an opening to an interior frame space that is essentially concentric with the vessel lumen. In some forms, the peripheral frame portions will be interconnected around the opening to provide a closed circumference frame opening. In these devices, one or more sheet or sheet-like materials will be coupled to the frame member such that when the frame moves from a first condition to an expanded second condition at a vascular site, the sheet material(s) will be forced into a blocking arrangement with regard to the frame opening. A sheet material may extend across the frame opening directly between the peripheral frame portions, or alternatively, may be located somewhat upstream or downstream of the frame opening when the device is deployed.

Figure 5A:
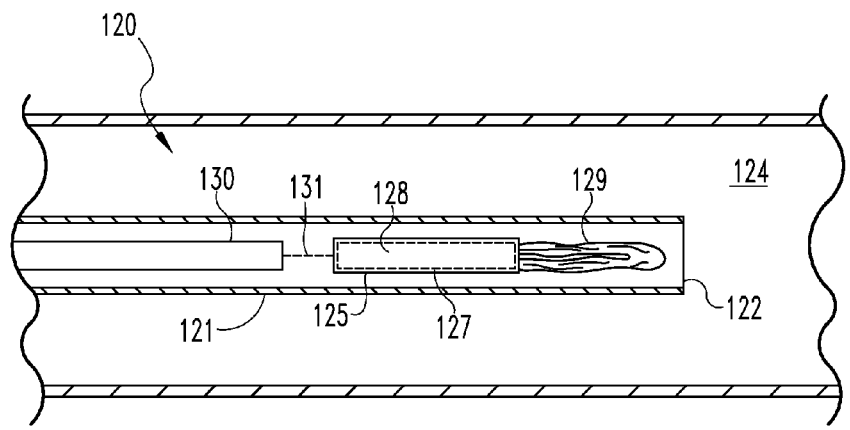
FIG. 5A provides a partial, side view of another inventive medical product being used to deploy an occlusion device in a vascular vessel.

FIG. 5A shows a medical product 120 according to another embodiment of the present invention after it has been advanced to a location in a vascular vessel 124. Medical product 120 includes a delivery sheath 121 having a lumen communicating with a distal end opening 122. Medical product also includes an occlusion device 125 which can exhibit a compact, first configuration for removably positioning the device in the delivery sheath lumen as shown.

Medical product 120 further includes a deployment member 130 that is translatable through the delivery sheath lumen. In some aspects, a deployment member is a simple pusher that can be used to push an occlusion device from a delivery sheath lumen. Additionally or alternatively, a deployment member may be equipped to somehow engage the occlusion device for moving the occlusion device with respect to the delivery sheath, and potentially also manipulating the occlusion device in the vascular vessel lumen during and/or after deployment. Illustratively, a pusher may provide a mechanism by which to grasp or otherwise grip or capture part of an occlusion device.

Though optional, medical product 120 includes a coupling element 131 that extends between the occlusion device and the deployment member. A coupling element of this sort, when incorporated into an inventive device, can include any suitable adaptation to enable the pusher and occlusion device to be temporarily connected or otherwise united with one another. These include but are not limited to those involving single- and multiple-part coupling mechanisms, grasping devices including lockable and non-lockable forceps, magnetic devices, energizable components, clasps, various bonding materials effective to bond two objects together, and combinations and variations thereof. In some preferred embodiments, a delivery device will include means for visualizing and identifying different device components and their surroundings during deployment.

Occlusion device 125 includes a frame member 127, an expandable occluding material 128, and a flexible sheet material 129. Although not necessary to broader aspects of the invention, in some instances, sheet material 129 will be made to extend distally from frame member 127 when housed in the delivery device lumen as shown in FIG. 5A, for example, by folding or otherwise collapsing the material out in front of the other device components.

Figure 5B:
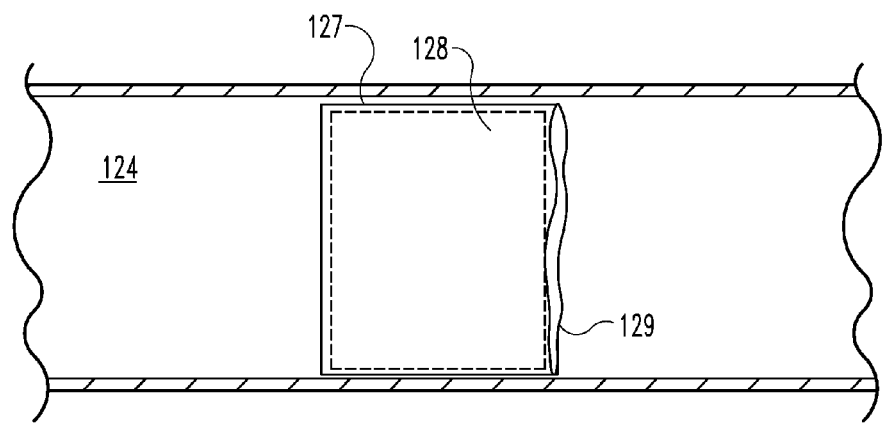
FIG. 5B provides a partial, side view of the occlusion device of FIG. 5A deployed in a vascular vessel.

Upon deployment from the delivery sheath lumen, occlusion device 125 is effective to expand to an expanded condition in the vascular vessel as shown in FIG. 5B. In this expanded condition, the occluding material is expanded toward the vessel walls so as to at least partially fill the vessel with an expanded material. Depending on the design and relative positioning of the other device components, the occluding material may contact a significant portion of the vessel walls when expanded. In this expanded condition, portions of the frame member, whether through self-expansion of the frame member and/or through the force of the expanding occluding material, move outward relative to their pre-deployment locations, with the frame member providing a framework in and/or around the expanded occluding material. In this specific illustrative embodiment, the frame member provides an open-ended, generally cylindrical structure when expanded, although frames having closed end(s) and non-cylindrical shapes can be utilized. As portions of the frame move toward the vessel walls, the corresponding attached sheet portions are pulled therealong into a blocking arrangement in the lumen.

Figure 6A:
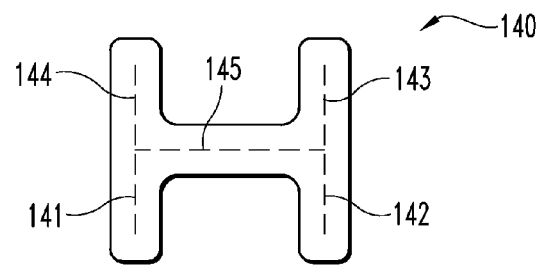
FIG. 6A is a front view of another inventive device.

The present invention provides several occlusion device embodiments having a framework positioned in and/or around an occluding material. These frameworks can have a variety of shapes and configurations as described elsewhere herein, and can be provided by one or more individual frame pieces. Referring now to FIG. 6A, shown is another inventive occlusion device 140 incorporating a framework 141 and a volumetrically expandable material 142. Framework 141 is substantially embedded within the expandable material 142, and includes a distal frame member 143, a proximal frame member 144 and a connector 145 extending therebetween. In this particular design, although not necessary to some broader aspects of the invention, the end pieces and connector are each separately formed and then later coupled to one another. This particular connector is formed with a length of wire or suture although a variety of other materials and single- or multiple-part objects having a variety of shapes (e.g., tube, spring, coil, chain links, braided material, etc.) for joining frame pieces together may be used.

Figure 6B:
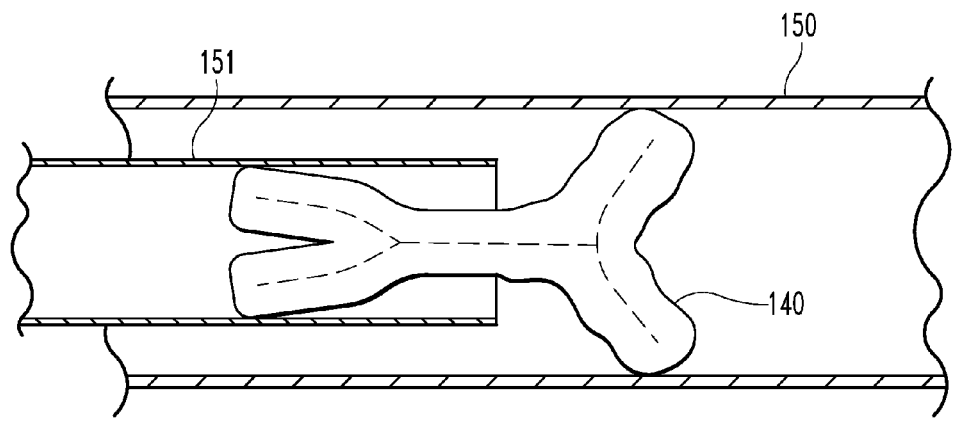
FIG. 6B shows the device of FIG. 6A being deployed from a delivery device into a vascular vessel.

Shown in a relaxed or unstressed condition in FIG. 6A, the frame ends have resiliency and can be bent and/or otherwise collapsed to attain a lower profile delivery configuration as shown in FIG. 6B. In this regard, connected frame pieces of this sort can be shaped and configured in a variety of manners to contribute to an overall device framework that is suitable for delivery of the device and for facilitating occlusion of a vessel once delivered. These include various three-dimensional shapes having rectilinear and/or curvilinear portions. Suitable three-dimensional rectilinear shapes can have any suitable number of sides, and can include, for example, cubes, cuboids, tetrahedrons, prisms, pyramids, wedges, and variations thereof. Suitable three-dimensional curvilinear shapes can include, for example, spheres, spheroids, ellipsoids, cylinders, cones, and any suitable variations thereof (e.g., a segment of a sphere, or a truncated cone, etc.). In this specific illustrative embodiment, the end pieces have general wheel or disc-like shapes although in an alternative design, as just one example, expandable frame members such as those depicted in FIG. 3A could be used. Further, the proximal and distal frame portions are formed with Nitinol although a variety of other materials may be used as well as described elsewhere herein. As viewed from the front as in FIG. 6A, the illustrative wheel-shaped ends, while not necessary to some broader aspects of the invention, both lie in a generally flat plane and extend in a generally perpendicular manner relative to the connector. These and other frame ends, when utilized in the present invention, can alternatively have non-planar features and/or can be oriented at an angle relative to the connector.

FIG. 6B shows a step in one illustrative inventive method in which device 140 is being deployed in a vascular vessel 150. The device 140 is shown with part of the device including its distal frame portion 143 extending from the distal, open end of a delivery cannula 151. A pusher or other similar device (not shown) may be used to force the device out of the delivery cannula. As illustrated, the disc-like frame ends have diameters that are slightly larger than that of the vascular vessel lumen so that as they expand upon exiting the delivery cannula, the relatively smaller diameter of the vessel prevents the frame ends from returning to their fully expanded conditions, thus causing the frame ends to apply a degree of radial force to the inside surface of the vessel wall to facilitate lodgment of the device in the vessel. Additionally or alternatively, in some instances, the device will incorporate one or more anchoring adaptations as described elsewhere herein that can embed in the vessel wall upon deployment. While having somewhat oversized diameters in this specific illustrative embodiment, the various disc and other non-disc frame pieces contemplated in some broader aspects of the invention can have dimensions that are slightly smaller or larger or equal to the diameter of a vessel to be occluded.

A framework, or any piece thereof, can be made to reside in and/or around an occluding material in any suitable manner. In some aspects, an occluding material component will be formed separately from a frame component. Suitable formation techniques include but are not limited to extrusion, using a mold or form, construction around a mandrel, and/or combinations or variations of these techniques or other known formation techniques. After the occluding material component is formed, a frame piece is incorporated into it, whether as a complete framework or as a component of a framework. In some other aspects, an occluding material component is constructed so as to already incorporate one or more frame pieces, for example, by forming a volumetrically expandable occluding material around a frame component inside a mold or form.

Figure 6C:
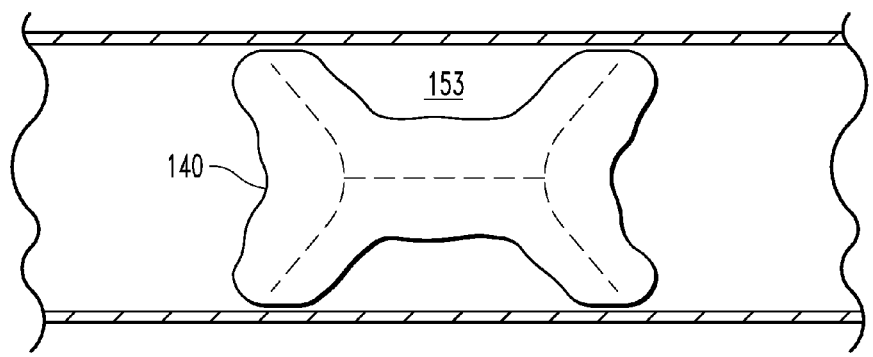
FIG. 6C shows the device of FIG. 6A deployed in a vascular vessel.

Occluding material 142 in this particular embodiment is a highly expandable remodelable ECM material although it could be provided by one or more of a variety of materials as discussed herein. Occluding material 142, which essentially surrounds all portions of the framework 141, is effective to volumetrically expand around the framework at the vascular site so as to provide a frame-supported, highly volumetrically expanded material in the vessel. This expansion, in some instances, will essentially fill a longitudinal segment of the vessel with a highly volumetrically expanded material having one or more frame pieces embedded therein. FIG. 6C shows device 140 after it has been fully deployed from the delivery cannula into the vascular vessel lumen, with the occluding material fully volumetrically expanded. In this specific illustrative embodiment, each volumetrically expanded end portion of the device provides a substantial occlusion of the vascular vessel, with an intermediate space 153 occurring around the connector between the two end portions. Although a device can be configured so that this intermediate space is too occupied by portions of the occluding material 142 upon full expansion, when a fully expanded device provides such a space, it can optionally be filled with one or more space filling substances or materials as described elsewhere herein. In alternative designs, a substantial portion of a connector such as connector 145 is not embedded in an occluding material.

Optionally, a variety of materials and substances can be placed into spaces in and/or around a construct such as intermediate space 153 prior to finally completing an implantation procedure. These include various space filling materials such as remodelable or resorbable materials, for example, a comminuted, fluidized, and/or gelatinous remodelable material as described elsewhere herein, or other substances (e.g., in the form of fluids, pastes, gels, sponges, powders, tissue fragments, segments, strips, layers, etc.), therapeutic agents, e.g. any drug such as an antibiotic, antimicrobial agent, or the like as discussed elsewhere herein including any material conducive to achieving chronic occlusion of a vascular vessel of interest. Other options include but are not limited to blood, polymer, contrast medium, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof. As well, the exterior and/or other regions of an occlusion device might be coated with one or more materials or substances such as a drug coating, or the like.

In this regard, in some inventive embodiments, one or more agents or other substances (as described herein) can be conjunctively or cooperatively emplaced within a patient with one or more occlusive implants as are discussed herein. Cooperative emplacement can include the contact of patient tissue with agents before, after, and/or while the occlusive device is implanted in the patient. Such tissue contact of agents can occur in those areas that will become or are in contact with one or more occlusive devices and/or are adjacent to or near the implant or prospective implant location. For example, the agents can be delivered into the patient through a cannulated lumen, such as before an occlusive device is implanted, or can be injected into a patient through a needle and syringe, such as after an occlusive device is implanted. In additional embodiments, the agents can be contained within or on the occlusive device, such as by being applied to an occlusive construct by a physician before implantation occurs, and/or by being doped, bonded, or otherwise contained within a dry occlusive construct, such as can be achieved by soaking a construct in one or more agents and thereafter drying and packaging the construct.

In certain embodiments, a supplemental material will include a substance that is capable of bringing about or inducing constriction, spasm, or closure in a bodily vessel of a patient and/or causing the de-epithelialization or inflammation (either dilative or constrictive), and/or otherwise initiating a healing response in patient tissue, such as a wall segment of a venous vessel. Such agents can include any suitable vasoconstrictive agent, sclerosive agent, thrombogenic agent, inflammatory agent, hypercoagulable agent, or any suitable combination of one or more of any of the above or other suitable agents. For example, suitable vasoconstrictive agents can include any suitable alpha adrenergic direct or indirect agonist, such as norepinephrine, epinephrine, phenylephrine, and/or cocaine, or lidocaine, hypertonic saline, or any suitable combination thereof. Illustrative sclerosive agents can include, for example, polidocanol, sodium tetradecyl sulfate, e.g. SOTRADECOL®, morrhuate sodium, ethanolamine oleate, tetradecyl sulfate, tetracycline, glycerin, hypertonic glucose, talc, acetic acid, alcohol, bleomycin, picibanil, ethibloc, deoxycycline, and/or any suitable microfoam that contains a sclerosive agent, such as VARISOLVE®, manufactured by Provensis, Ltd. of London, England, or any other suitable agent as disclosed in U.S. Pat. Nos. 5,676,962 and/or 6,572,873, for example. In some aspects, an anesthetic agent may be added to a sclerosant agent mixture or other fill material.

Additionally, a supplemental material, including, e.g. remodelable ECM fill materials, can include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within a fill material, such that, for example, the location of the fill material within a patient's body can be detected.

Figure 7A:
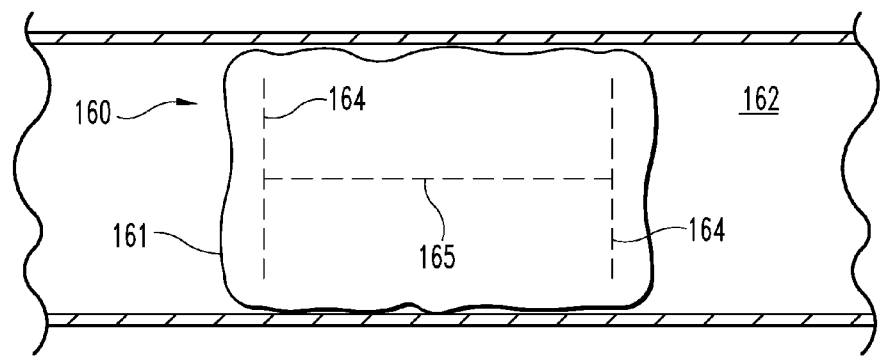
FIG. 7A shows another inventive device deployed in a vascular vessel.

In FIG. 7A, another deployed inventive occlusion device 160 is shown providing an expanded occluding material 161 along a longitudinal segment of a vessel lumen 162 so as to occlude the lumen segment. A framework, which could be adapted from any of those described herein, is located in the expanded material. The framework includes opposing ends 164 having diameters slightly smaller than that of the vessel lumen, and a connector 165 connecting the opposing ends. At least one of the frame ends, and in certain embodiments both of the frame ends, can optionally comprise one or more wires (e.g., formed with Nitinol) that extend away from the connector. Such wires can extend from the connector in a variety of directions, at a variety of angles, etc. Groups of wires can provide random or non-random shapes and patterns when the frame is in an unstressed condition.

In certain aspects, the present invention provides frame-embedded devices that are deliverable to a bodily site in a compressed condition. Such devices include an expandable construct (e.g., a remodelable ECM construct) that is effective to volumetrically expand at the site so as to provide a volumetrically expanded mass of material at the site. Such devices further include a single- or multiple-piece frame that is at least partially embedded in the expandable construct. Various types of frame and frame-like elements can be utilized in this regard. In some forms, a frame member will include a filament or wire body or other similar frame or frame-like member that is rigid, malleable, semi-flexible, or flexible. In this regard, a device such as that shown in FIG. 7A could be constructed without the opposing end pieces 164 so as to leave a single piece of wire embedded in a highly volumetrically expandable remodelable ECM construct. If deformable, this sort of wire could then be constructed to exhibit a variety of shapes and configurations when in non-deformed and deformed conditions.

In some forms, an embedded frame element will be at least somewhat deformable so that it can be compressed or compacted into a lower-profile condition for delivering the device into the body, for example, in a catheter lumen. Thereafter, when no longer constrained by the catheter, the frame element will attempt to transform back to its pre-deformed shape at the bodily location. This can be used, in some arrangements, to at least somewhat affect where in the body the associated volumetrically expandable material will be positioned after the device is deployed. Embedded frame members, in some embodiments, can be designed to move between a first condition and one or more other conditions, for example, in the case of a frame that is compactable to a compacted, first condition, and when in this compacted condition, is then expandable to an expanded, second condition. In this regard, an overall device can include a volumetrically expandable material that works to volumetrically expand upon deployment in the body, while also having an embedded frame element that simultaneously works to expand on its own (e.g., radially) while interacting with the material that is volumetrically expanding in and/or around it. In forms where a frame has the capacity to expand, these frames can include those that are considered self-expanding and those that require at least some manipulation in order to expand. In certain forms, an embedded resilient frame member can be provided in a relaxed condition. The frame while embedded in an expandable material can then be deformed (e.g., collapsed, compressed, etc.) from this relaxed, first condition to a deformed, second condition and held there. In this deformed, second condition, the resilient frame is then poised to essentially return to its relaxed, first condition.

Figure 7B:
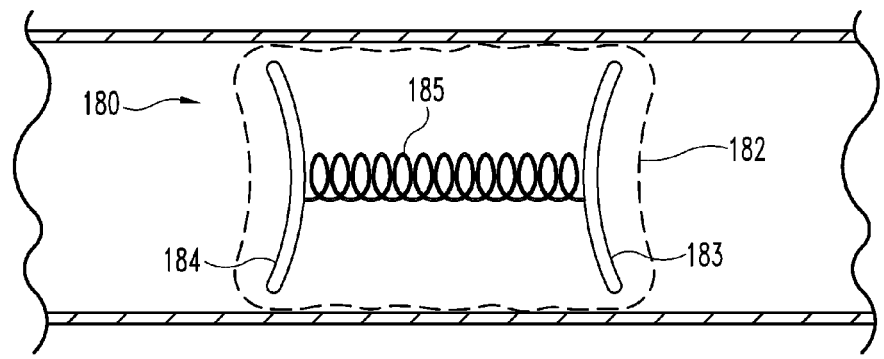
FIG. 7B shows yet another inventive device deployed in a vascular vessel.

Referring now to FIG. 7B, shown is another inventive occlusion device 180 incorporating a framework that is substantially embedded within an expandable occluding material 182. Framework includes a distal frame portion 183, a proximal frame portion 184 and a connector 185 extending therebetween. In this particular design, the end portions have a convexo-concave shape (e.g., formed with a resorbable or other synthetic material), and the connector (e.g., formed with Nitinol) is a spring or coil. Connectors having spring or spring-like properties are advantageous in certain embodiments of the invention, for example, to enhance the delivery characteristics of the device as well as its ability to anchoring itself in the vascular vessel upon delivery. Spring or spring-like properties, when incorporated into a connector or other frame component such as a frame end, can help provide a flexible yet durable lodgment of an occlusion device in a vascular vessel. The bias of a connector, in some forms, will help maintain the radial force being directly or indirectly applied by connected end portions to the inner surface of a vessel wall.

Turning now to a more detailed discussion of materials that can be used in the manufacture of certain inventive devices, occluding devices of the invention can incorporate naturally derived and/or non-naturally derived materials. Illustratively, sheet form and non-sheet form materials useful in the invention such as occluding material 32 and sheet 33 may comprise one or more of a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, inventive devices can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

In certain embodiments, one or more device components will be comprised of a remodelable material. Particular advantage can be provided by devices that incorporate a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within vessels and other bodily spaces into which inventive devices are implanted.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

When used in the invention, ECM materials may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

In certain aspects, the invention utilizes an occluding device that includes a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating at about room temperature (about 25° C.) or with cooling. Relatively low temperature conditions also, of course, include lyophilization conditions.

When utilized in the invention, expandable materials can be formed with one or more of a variety of materials including some that are naturally derived and some that are non-naturally derived. Illustratively, three-dimensionally stable porous matrix materials, such as resilient foam or sponge form materials, can be incorporated into an inventive product. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in certain embodiments of the present invention can be formed by providing a liquid solution or suspension of a matrix-forming material, and causing the material to form a porous three-dimensionally stable structure; however, a sponge or foam material can be formed using any suitable formation method, as is known in the art.

In additional embodiments, graft constructs useful in the invention can include ECM materials and other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of an occluding element useful in certain aspects of the invention. Illustratively, the expanded material can be enriched with bioactive components, dried, and/or molded, etc., in the formation of a desirably shaped and configured graft construct. In certain embodiments, a dried graft body formed with the expanded ECM material can be highly compressible (or expandable) such that the material can be compressed for delivery, such as into a vascular vessel, and thereafter expand upon placement therein, so as to fully or partially occlude the vessel, and in some cases, fully prevent the flow of fluid through the vessel.

Expanded collagenous or ECM materials can be formed by the controlled contact of a collagenous or ECM material with an aqueous solution or other medium containing sodium hydroxide Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 M to about 4 M, with a concentration of about 1 M to about 3 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 3 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of occluding elements useful in certain aspects of the invention. It can further allow for the preparation of constructs that are highly compressible and which expand after compression. Such properties can be useful, for example, when the prepared construct is to be compressed and loaded into a deployment device (e.g. a lumen of a delivery catheter) for delivery into a bodily vessel, and thereafter deployed to expand in the vessel.

After such alkaline treatments, the material can be isolated from the alkaline medium and processed for further use. Illustratively, the collected material can be neutralized and/or rinsed with water to remove the alkalinity from the material, prior to further processing of the material to form a device component.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans. This may be true for other processing techniques as discussed herein, such as the controlled treatment of the material with a detergent.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression similar to a non-expanded material.

Expanded collagenous materials can be used in preparing a wide variety of occluding components useful in the invention. Methods for preparing such components can include contacting an ECM or other collagenous starting material with an alkaline substance in an amount effective to expand the material, comminuting the expanded material e.g., with a blender, casting or otherwise forming the blended expanded collagenous material into a particular shape, and lyophilizing the expanded material to form a dried construct. Alternatively, one or more sheets of an expanded remodelable collagenous material can be formed. In one embodiment, one or more sheets of an expanded remodelable collagenous material can be stacked, frozen and lyophilized to form a multi-laminate expanded remodelable collagenous material. One or more sheets can be rolled to form a generally cylindrical, conical or otherwise shaped construct, if desired.

In certain embodiments, an occluding material includes a flowable or otherwise conformable collagenous ECM material that is at least partially solubilized or otherwise denatured or disassembled relative to its native collagenous structure. Illustratively, a suitable conformable ECM material may comprise an ECM material paste, a fluidized ECM material, and/or gelatinous ECM material. In some forms, an ECM material comprises a flowable composition comprising solubilized or suspended ECM material such as an ECM hydrolysate material. Suitable flowable, remodelable ECM materials for use in this aspect of the invention can be prepared, for example, as described in U.S. Pat. Nos. 5,275,826, 5,516,533, 6,206,931, and/or 6,444,229 or in International Publication No. WO2005020847 (Cook Biotech Incorporated) published Mar. 10, 2005, which are each hereby incorporated by reference in their entirety.

Flowable or otherwise conformable ECM materials when used in the present invention can be prepared to have desirable properties for handling and use. For example, a fluidized ECM hydrolysate can be prepared in an aqueous medium, which can thereafter be caused or allowed to form a gel for use in the invention. Such prepared aqueous mediums can have any suitable level of ECM hydrolysate therein. Typically, the ECM hydrolysate will be present in the aqueous medium at a concentration of about 2 mg/ml to about 200 mg/ml, more typically about 8 mg/ml to about 120 mg/ml, and in some embodiments about 10 mg/ml to about 75 mg/ml. In certain illustrative forms, the aqueous ECM hydrolysate composition to be gelled will have an injectable character, for example, by injection through a needle having a size in the range of 18 to 31 gauge (internal diameters of about 0.047 inches to about 0.004 inches). Further, flowable ECM compositions can be prepared so that in addition to neutralization, heating to physiologic temperatures (such as 37° C.) will substantially reduce the time needed to solidify or otherwise immobilize the ECM material.

While useful to provide occlusions and blockages in arteries and veins and other openings and passageways in the vasculature, inventive devices can be adapted and used to occlude, block, fill, etc. a variety of suitable passageway and open spaces in the body including those in non-vascular locations. In some instances, an inventive device will be configured for placement in a naturally occurring location in the body, for example, in a native lumen or other open space in a bodily system, e.g., in an organ or other component of the circulatory, respiratory, digestive, urinary and reproductive, sensory, or endocrine systems. In certain aspects, a space to be occluded is one that exists naturally in the body but relates to a disease, defect, deformation, etc. Alternatively, an opening or passage to be filled may be one resulting from an intentional or unintentional trauma to the body including but not limited to some relating to vehicular accidents, gunshots and other similar wounds, etc., as well as some formed by passage of a medical instrument (e.g., a needle, trocar, etc.) through cutaneous, subcutaneous, and/or intracutaneous tissue.

The present invention also provides, in certain aspects, medical products that include a radiopaque element such as but not limited to a radiopaque coating, attached radiopaque object, or integrated radiopaque substance. Any suitable radiopaque substance, including but not limited to, tantalum such as tantalum powder, can be incorporated into a medical product of the invention. Other radiopaque materials comprise bismuth, iodine, and barium, as well as other suitable markers.

In additional embodiments, the present invention provides medical products that include means or devices as described herein for delivering occlusion devices into and otherwise providing occlusion in the vasculature, and written materials including instructions for use of the means or devices to deliver occlusion devices into and otherwise provide occlusion in the vasculature. The products can include the means or devices packaged together with the instructions, e.g. in sterile medical packaging. Related embodiments of the invention include methods for distributing such means or devices, or otherwise conducting business, which include distributing such means or devices for delivering occlusion devices into and otherwise providing occlusion in the vasculature, and also distributing information relating the use of such means or devices for delivering occlusion devices into and otherwise providing occlusion in the vasculature. Such information can be distributed packaged with the means or device, or separately, e.g. including information or instructions available on a communication network, including a global computer communication network such as the internet.

The present invention also provides, in certain aspects, a line of medical products, wherein a medical product of the invention includes one or more devices, apparatuses or systems of the invention in a sealed package. In some forms of the invention, medical products are provided that include one or more occlusion devices such as any of those described herein, and potentially also a suitable delivery apparatus or other delivery instrumentation, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additionally, the package can include indicia to communicate the contents of the package to a person, machine, computer, and/or electronic device. Such indicia may include the dimensions of, the type of materials used to form, and/or other useful information regarding the contents of the package. In certain embodiments, the contents are packaged for sale with instructions for use. For example, in certain preferred embodiments, a medical product includes at least one occlusion device and delivery instrumentation sealed within a sterile package, wherein the packaging can have visible indicia identifying the contents as suitable for providing occlusion in the vasculature, and/or can contain or otherwise be associated with printed materials identifying the contents as such and including information concerning their use.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A device for occluding a vascular vessel having a vessel lumen, comprising:

a frame movable between a first condition suitable for transluminal vascular delivery to a vascular site for providing an occluding device, and an expanded second condition adapted for deployment at the vascular site, the frame having a proximal end longitudinally spaced from a distal end and including a plurality of elongate arms that emanate from a common centralized region at the proximal end of the frame and extend distally to the distal frame end, wherein the distal frame end includes free distal ends of said arms, the expanded second condition including an expanded frame segment in which the free distal ends of the arms are outwardly displaced relative to the common centralized region and in which side openings in the frame occur between adjacent arms, the expanded frame segment being spaced distally from the common centralized region, the expanded frame segment defining an interior region bounded by the frame and occurring between the free distal ends of the arms and the common central region, and the expanded frame segment defining an open distal end of the frame occurring between the free distal ends of the arms;

a flexible sheet material coupled to the frame such that when the frame is in the expanded second condition at the vascular site the sheet material is positioned in the vessel lumen so as to provide a deployed sheet material segment blocking the vessel lumen, the deployed sheet material segment defining an interior surface longitudinally spaced from and facing toward the common centralized region of the frame; and an expandable remodelable occluding material located at least partially in the interior region of the frame and longitudinally positioned entirely between the interior surface of the deployed sheet material segment and the common centralized region when the frame is in the second expanded condition at the vascular site, the expandable remodelable occluding material effective to expand at the vascular site so as to provide an expanded remodelable material, wherein the expandable remodelable occluding material is effective upon implantation to become broken down and replaced by new patient tissue at the vascular site for facilitating occlusion of the vascular vessel.

2. The device of claim 1, wherein said expandable material is effective to expand at the vascular site so as to provide said expanded material extending through said side openings in the frame for contacting patient tissues at the vascular site.

3. The device of claim 1, wherein the expandable occluding material is located in the interior region of the frame so as to be effective to at least partially move the frame between the first condition and the expanded second condition upon expansion at the vascular site.

4. The device of claim 1, wherein the sheet material is coupled to the frame so as to include portions located between the expanded frame segment and inner wall surfaces of the vascular vessel when the frame is in the expanded second condition at the vascular site.

5. The device of claim 1, wherein the expandable occluding material is located in the interior region of the frame so as to position the expanded frame segment between the occluding material and inner wall surfaces of the vascular vessel when the frame is in the expanded second condition at the vascular site.

6. The device of claim 1, wherein the expanded frame segment includes a conical portion.

7. The device of claim 1, wherein the expanded frame segment includes a bulbous portion.

8. The device of claim 1, wherein the expandable occluding material is located in the interior region of the frame so as to include portions positioned externally of the frame when the frame is in the expanded second condition at the vascular site.

9. The device of claim 1, wherein the flexible sheet material is coupled to the frame so as to be drawn across the vascular vessel lumen when the frame moves from the first condition to the expanded second condition at the vascular site to provide said deployed sheet segment.

10. The device of claim 1, wherein said flexible sheet material is a remodelable sheet material.

11. A device for occluding a vascular vessel having a vessel lumen, comprising:
a frame movable between a first condition suitable for transluminal vascular delivery to a vascular site for providing an occluding device, and an expanded second condition adapted for deployment at the vascular site, the expanded second condition including a first frame end longitudinally spaced from a second frame end, the first frame end defining a first frame perimeter having an opening extending across the vessel lumen when the frame is deployed at the vascular site, and the frame defining side openings when in the second expanded condition;
a flexible remodelable sheet material coupled to the frame such that when the frame is in the expanded second condition at the vascular site the sheet material provides a deployed sheet material segment positioned across the first frame perimeter opening to block the vessel lumen but leaves at least a portion of the side openings uncovered by the sheet material, the deployed sheet material segment defining an interior surface longitudinally spaced from and facing toward the second frame end; and
an expandable remodelable material longitudinally positioned entirely between the interior surface of the deployed sheet material segment and the second frame end when the frame is in the expanded second condition and at least partially within an interior region of the frame with exposure to regions outside the frame through side openings in the frame, the expandable remodelable material effective to expand at the vascular site so as to provide an expanded material at the vascular site that contacts inner wall surfaces of the vascular vessel through said side openings, and wherein the expandable remodelable material is effective upon implantation to become broken down and replaced by new patient tissue at the vascular site for facilitating occlusion of the vascular vessel.

12. The device of claim 11, wherein said opening of said first frame perimeter is in communication with the interior region of the frame.

13. The device of claim 12, wherein said opening of said first frame perimeter is located at a distal end of the frame.

14. The device of claim 11, wherein:
the frame includes a plurality of elongate arms that emanate from a common centralized region at the first frame end and extend to the second frame end, wherein the second frame end includes free ends of said arms; and
the expanded second condition of the frame includes an expanded frame segment in which the free ends of the arms are outwardly displaced relative to the common centralized region and in which openings in the frame occur between adjacent ones of the arms.

15. The device of claim 14, wherein the expandable remodelable occluding material comprises collagen.

16. The device of claim 15, wherein the expandable remodelable occluding material comprises an expanded extracellular matrix material.

17. The device of claim 15, wherein the expandable remodelable occluding material is comprised of a dried graft body formed with an expanded extracellular matrix material.

18. A device for occluding a vascular vessel having a vessel lumen, comprising:
a frame having a distal frame end longitudinally spaced from a proximal frame end, the frame movable between a first condition suitable for transluminal vascular delivery to a vascular site for providing an occluding device, and an expanded second condition adapted for deployment at the vascular site, the frame having an interior space that expands as the frame moves from the first condition to the second condition such that the expanded second condition includes an expanded interior space adjacent to a distal frame opening defined at the distal frame end, the distal frame opening extending across the vessel lumen when the frame is deployed to the expanded second condition at the vascular site, and the frame defining side openings when deployed to the expanded second condition at the vascular site;
an expandable remodelable occluding material located at least partially within the interior space of the frame and effective to expand at the vascular site so as to provide an expanded material extending through the side openings of the frame for contacting inner wall surfaces of the vascular vessel at the vascular site, wherein the remodelable occluding material is effective upon implantation to contact the inner wall surfaces of the vascular vessel and to become broken down and replaced by new patient tissue at the vascular site for facilitating occlusion of the vascular vessel;
a flexible sheet material coupled to the frame such that when the frame is in the expanded second condition at the vascular site the sheet material provides a deployed sheet segment positioned across the distal frame opening and defining an interior surface longitudinally spaced from and facing toward the proximal frame end; and
the expandable remodelable occluding material, when the frame is in the expanded second condition, longitudinally positioned entirely between the interior surface of the deployed sheet segment and the proximal frame end.

19. The device of claim 18, wherein the distal frame opening and at least part of the expanded interior space have essentially the same diameter.

20. The device of claim 18, wherein the flexible sheet material includes a harvested extracellular matrix sheet material.

21. The device of claim 18, wherein the flexible sheet material comprises a synthetic polymeric material.

22. The device of claim 18, wherein:
the frame includes a plurality of elongate arms that emanate from a common centralized region at the proximal frame end and extend to the distal frame end, wherein the distal frame end includes free ends of said arms; and
the expanded second condition of the frame includes an expanded frame segment in which the free ends of the arms are outwardly displaced relative to the common centralized region and in which openings in the frame occur between adjacent ones of the arms.

23. The device of claim 22, wherein the expandable remodelable occluding material comprises collagen.

24. The device of claim 23, wherein the expandable remodelable occluding material comprises an expanded extracellular matrix material.

25. The device of claim 22, wherein the expandable remodelable occluding material is comprised of a dried graft body formed with an expanded extracellular matrix material.

26. A device for occluding a vascular vessel, comprising:
a frame movable between a first condition suitable for transluminal vascular delivery to a vascular site for providing an occluding device, and an expanded second condition adapted for deployment at the vascular site, the frame having a first end and a second end and including a plurality of elongate arms that emanate from a common centralized region at the first end of the frame and extend to the second frame end, wherein the second frame end is longitudinally spaced from the first frame end and includes free ends of said arms, the expanded second condition including an expanded frame segment in which the free ends of the arms are outwardly displaced relative to the common centralized region and in which side openings in the frame occur between adjacent ones of said arms;
a flexible sheet material coupled to the frame such that when the frame is in the expanded second condition at the vascular site the sheet material provides a deployed sheet material segment positioned in the vascular vessel lumen so as to block fluid flow through the lumen and so as to define an interior surface longitudinally spaced from and facing toward said common centralized region; and
an expandable occluding material longitudinally positioned entirely between the interior surface of the deployed sheet material segment and the common centralized region and at least partially in an interior region of the frame when the frame is in the expanded second condition, the expandable occluding material effective to expand when the device is implanted at the vascular site.

27. The device of claim 26, wherein the expandable occluding material comprises a collagenous material or a bioresorbable synthetic polymeric material.

28. The device of claim 26, wherein the frame is self-expandable.

29. The device of claim 26, wherein the occluding material is receptive to tissue ingrowth.

30. The device of claim 26, wherein the occluding material comprises a remodelable material that is broken down and replaced by new patient tissue upon implantation at the vascular site.

31. The device of claim 30, wherein the flexible sheet material comprises a harvested collagenous extracellular matrix material.

* * * * *